(12) United States Patent  
Czaplewski et al.

(10) Patent No.: US 11,896,515 B2
(45) Date of Patent: Feb. 13, 2024

(54) CONVEX OSTOMY BARRIER

(71) Applicant: Hollister Incorporated, Libertyville, IL (US)

(72) Inventors: Gregory J. Czaplewski, Glendale Heights, IL (US); Anthony Scalise, Plainfield, IL (US); Tuan Tran, Genoa City, WI (US); Peter L Visconti, Gurnee, IL (US); Kenneth Nielsen, Ålsgårde (DK); Jon Z. Lugenbill, Warrenville, IL (US); Daniel A. March, Lake Villa, IL (US)

(73) Assignee: Hollister Incorporated, Libertyville, IL (US)

(*) Notice: Subject to any disclaimer, the term of this patent is extended or adjusted under 35 U.S.C. 154(b) by 486 days.

(21) Appl. No.: 16/341,227

(22) PCT Filed: Nov. 15, 2017

(86) PCT No.: PCT/US2017/061674
§ 371 (c)(1),
(2) Date: Apr. 11, 2019

(87) PCT Pub. No.: WO2018/093815
PCT Pub. Date: May 24, 2018

(65) Prior Publication Data
US 2019/0254864 A1    Aug. 22, 2019

Related U.S. Application Data

(60) Provisional application No. 62/422,232, filed on Nov. 15, 2016.

(51) Int. Cl.
| | |
|---|---|
| *A61F 5/443* | (2006.01) |
| *A61F 5/44* | (2006.01) |
| *A61F 5/445* | (2006.01) |
| *A61F 5/451* | (2006.01) |

(52) U.S. Cl.
CPC ............ *A61F 5/443* (2013.01); *A61F 5/4404* (2013.01); *A61F 5/445* (2013.01); *A61F 5/451* (2013.01)

(58) Field of Classification Search
CPC ........ A61F 5/443; A61F 5/4404; A61F 5/445; A61F 5/451; A61F 2005/4483;
(Continued)

(56) References Cited

U.S. PATENT DOCUMENTS

| | | | |
|---|---|---|---|
| 4,610,676 A * | 9/1986 | Schneider | A61F 5/448 604/339 |
| 5,125,917 A | 6/1992 | Whealin | |
| 5,718,696 A * | 2/1998 | Kollerup | A61F 5/443 604/339 |

FOREIGN PATENT DOCUMENTS

| | | | |
|---|---|---|---|
| DE | 202005015157 U1 | 5/2006 | |
| EP | 0479573 A1 | 4/1992 | |
| EP | 0631498 A1 * | 1/1995 | ............ A61F 5/448 |
| EP | 0650709 A1 | 5/1995 | |

(Continued)

OTHER PUBLICATIONS

International Preliminary Report on Patentability issued by International Bureau in connection with PCT/US2017/061674 dated May 21, 2019.

(Continued)

*Primary Examiner* — Nicholas J. Weiss
*Assistant Examiner* — Brandon W. Levy
(74) *Attorney, Agent, or Firm* — Levenfeld Pearlstein, LLC (57) ABSTRACT

A convex ostomy barrier includes a skin barrier, an inlet opening for receiving a stoma, and a convex insert. The convex insert includes an inner flange, an outer flange, and a middle portion arranged therebetween. The middle portion includes a pouch side surface for attaching a flange, a core-out portion configured to improve the flexibility of the (Continued)

convex insert, and a skin barrier support structure for supporting the skin barrier.

16 Claims, 11 Drawing Sheets

(58) Field of Classification Search
CPC .................. A61F 5/448; A61F 5/4408; A61F 2005/4486; A61F 5/449; A61F 2005/4495; A61F 5/44; A61F 13/45; A61L 24/00; A61L 2400/14
See application file for complete search history.

(56) References Cited

FOREIGN PATENT DOCUMENTS

| GB | 2181652 A | * | 4/1987 | ............. A61F 5/448 |
| WO | 2012079592 A1 | | 6/2012 | |

OTHER PUBLICATIONS

Extended European Search Report issued by ISA/EPO in connection with EP Patent Application No. 21184581.3 dated Oct. 26, 2021.
International Search Report issued by ISA/EPO in connection with PCT/US2017/061674 dated Aug. 16, 2018.
Written Opinion issued by ISA/EPO in connection with PCT/US2017/061674 dated Aug. 16, 2018.
Opposition filed at EPO against EP Patent No. 3541331 dated May 25, 2022.

* cited by examiner

CONVEX OSTOMY BARRIER

This is a National Stage Application of International Patent Application No. PCT/US2017/061674, filed Nov. 15, 2017, which claims the benefit of and priority to U.S. Provisional Application No. 62/422,232, filed Nov. 15, 2016, the entirety of which are incorporated fully herein by reference.

BACKGROUND

The following description generally relates to ostomy appliances, and in particular, to an ostomy barrier.

Ostomy pouches for collecting bodily waste are used by individuals who have had surgery such as a colostomy, ileostomy, or urostomy. Two common types of ostomy pouch systems are available, to wit, a one-piece pouch system and a two-piece pouch system. In a one-piece pouch system, an ostomy barrier is permanently attached to a pouch. In such a one-piece pouch system, the entire pouch system including the ostomy barrier is removed when a user wants to replace the pouch.

In a two-piece pouch system, a pouch and an ostomy barrier are provided as two separate devices. The two-piece pouch system typically includes a pair of coupling rings, one of which is fixedly attached to the ostomy barrier, while the other is attached to the pouch. The coupling rings are configured to mate with each other, such that the pouch may be securely and removeably attached to the ostomy barrier by engaging the coupling rings together. In use, the ostomy barrier is first attached to a user, and the pouch is secured to the faceplate by engaging the coupling rings together. Thus, two-piece pouch systems allow a user to remove and replace a pouch without removing the ostomy barrier from the user. This can help to reduce the discomfort and irritation associated with removing skin barrier adhesive from user's skin Ostomy barriers are configured to seal against peristomal skin surfaces and protect the peristomal surfaces from exposure to stomal effluent. However, the topography of stomas and peristomal surfaces surrounding stomas varies among patients, and sealing an ostomy appliance against such different peristomal surfaces and stomas remain as an area for further improvements. A person having a stoma that is flush or recessed may find that applying external support or pressure from a barrier in the peristomal region aids in directing the discharge of effluent from the stoma directly into the ostomy pouch. Accordingly, the effectiveness of an adhesive seal between the ostomy barrier and the peristomal skin surface (i.e., a seal formed by the adhesive layer) may be prolonged.

The present disclosure provides an improved flexible convex barrier according to various embodiments.

BRIEF SUMMARY

In one aspect, a convex ostomy barrier for attaching an ostomy appliance to the peristomal skin surrounding a stoma is provided. The ostomy barrier may comprise a skin barrier including an adhesive, an inlet opening for receiving a stoma, and a convex insert arranged adjacent the skin barrier. The convex insert may have a convex ring-like body and include an inner flange, an outer flange, and a middle portion arranged therebetween. The middle portion may include a pouch-side surface, a core-out portion configured to improve the flexibility of the convex insert, and a skin barrier support structure for supporting the skin barrier. The inner flange and the outer flange may be arranged in different axial planes to define the convex ring-like body. The convex ostomy barrier may also comprise a flange including a body-side coupling ring attached to the pouch-side surface of the convex insert.

In an embodiment, the skin barrier support structure may include a plurality of support structures extending axially from a body-side of the radial wall, wherein the plurality of support structures form a split ring-like shape. Each of the plurality of support structures may be surrounded by the core-out portion and include a sloped body-side surface configured to support the skin barrier having a convex body-side surface.

In another embodiment, the core-out portion may be defined by a plurality of core-out windows, and the skin barrier support structure may include a plurality of ribs. The plurality of core-out windows and the plurality of ribs may be arranged, such that adjacent ribs are spaced apart from each other by a core-out window therebetween, and each of the core-out windows is defined by a radial wall, an axial wall, and the adjacent ribs. In such an embodiment, the convex insert may include about 8 ribs to about 30 ribs.

In an embodiment, the convex insert may include a radial wall radially extending from the outer flange toward the inlet opening, and an axial wall extending axially from the radial wall in a body-side direction, wherein the inner flange may extend from the axial wall toward the inlet opening. In such an embodiment, the outer flange, the middle portion, and the inner flange may be configured to provide a step-like protrusion in the body-side direction.

In any of the foregoing embodiments, the convex ostomy barrier may also include a tape. The convex insert may be attached to a pouch-side of the tape, and the skin barrier may be attached to a body-side of the tape. The outer flange may have a concave body-side surface configured to conform to a curved contour of a lower base section of a convex portion of the convex ostomy barrier. In such an embodiment, at least some portion of a body-side surface of the outer flange, the skin barrier support structure, or a body-side surface of the inner flange may be attached to the tape. Further, at least the body-side surface of the outer flange may be heat sealed to the tape.

In any of the foregoing embodiments, the middle portion of the convex insert may include a radial wall. In such an embodiment, the pouch-side surface of the middle portion may be defined on a pouch-side of the radial wall. Further, the flange may be attached to the convex insert via a flange film, in which the flange film is attached to the pouch side surface. The pouch side surface may be generally flat, and the flange film may be heat sealed to the pouch side surface.

In another aspect, a convex insert for an ostomy barrier having a convex ring-like body is provided. The convex insert may comprise an inlet opening, an inner flange, an outer flange, and a middle portion including a pouch-side surface, a core-out portion configured to improve the flexibility of the convex insert, and a skin barrier support structure. The inner flange and the outer flange may be connected by the middle portion and arranged in different axial planes to define the convex-ring like body.

In some embodiments, the convex insert may include a radial wall radially extending from the outer flange toward the inlet opening, and an axial wall extending axially from the radial wall in a body-side direction, wherein the inner flange extends from the axial wall toward the inlet opening. In such embodiments, the outer flange, the middle portion, and the inner flange may provide a step-like protrusion in the body-side direction. The pouch-side surface may be defined on a pouch-side of the radial wall.

In an embodiment, the skin barrier support structure may include a plurality of support structures extending axially from a body-side of the radial wall, wherein the plurality of support structures form a split ring-like shape. Each of the plurality of support structures may be surrounded by the core-out portion and include a sloped body-side surface.

In another embodiment, the core-out portion may be defined by a plurality of core-out windows, and the skin barrier support structure may include a plurality of ribs. The plurality of core-out windows and the plurality of ribs may be arranged, such that adjacent ribs are spaced apart from each other by a core-out window therebetween, and each of the core-out windows is defined by a radial wall, an axial wall, and the adjacent ribs.

In yet another embodiment, the skin barrier support structure may include a ring-like structure extending axially from a body-side of the radial wall, and the core-out portion may be defined by two ring-like core-out portions. In such an embodiment, the skin barrier support structure may be arranged between the two ring-like core-out portions and have a sloped body-side surface.

In an embodiment, the skin barrier support structure may include a plurality of rod-like structures or a plurality of tube-like structures extending axially from a body-side surface of the radial wall.

In another embodiment, the core-out portion may be defined by a plurality of openings in the middle section, and the skin barrier structure may be provided between the plurality of openings on the body-side of the middle portion.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Figure 1:
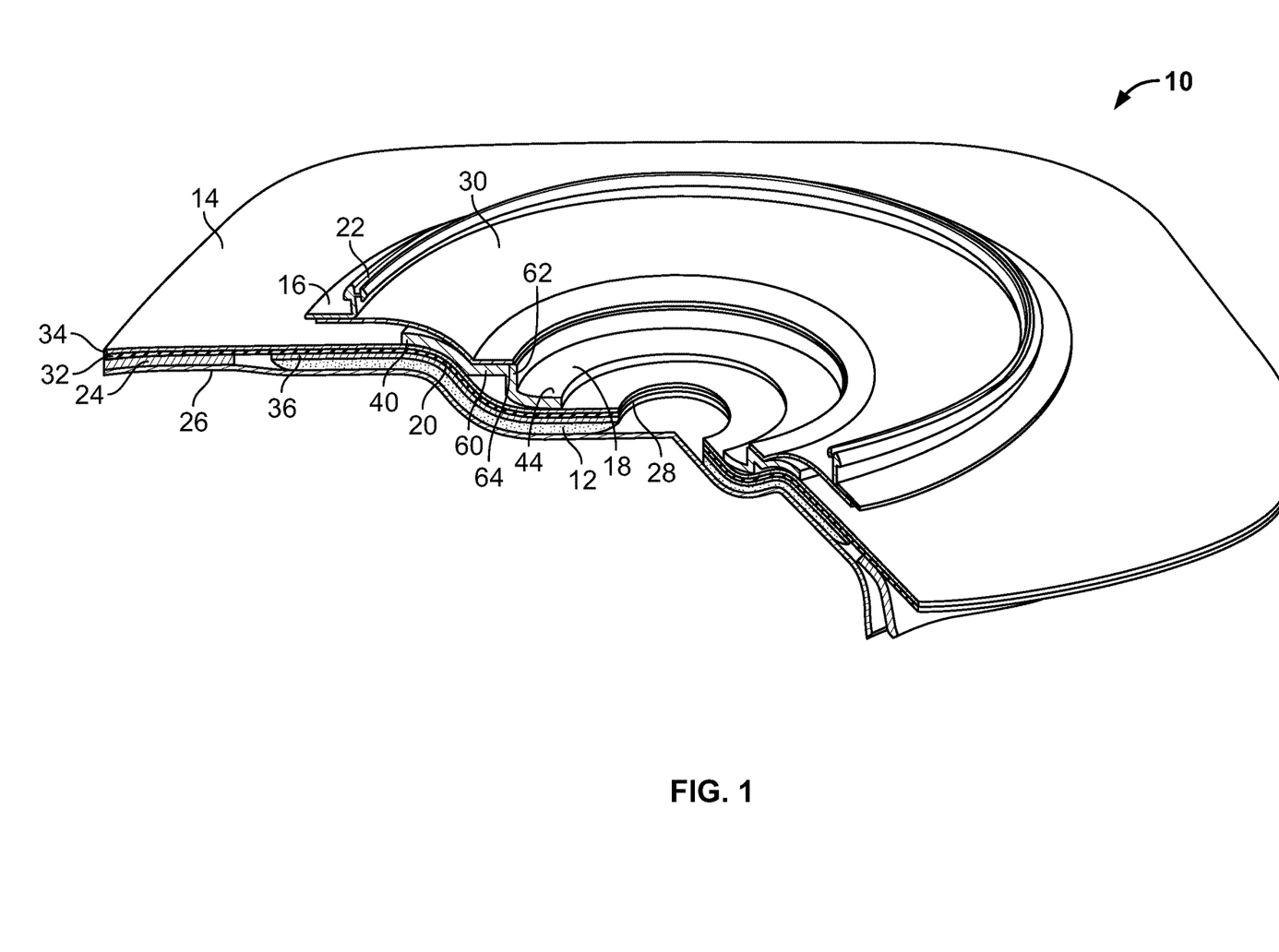
FIG. 1 is a perspective view of a convex ostomy barrier according to an embodiment with a portion removed to illustrate its layered structure.

Referring to FIG. 1, an ostomy barrier 10 according to an embodiment is shown with a portion removed and viewed from a pouch-side to illustrate a layered construction of the ostomy barrier 10. The ostomy barrier 10 may be configured as an ostomy barrier for a two-piece pouch system, and may generally include a skin barrier 12, a flange 16, a convex insert 18, release liners 24, 26, and an inlet opening 28 for receiving a stoma.

The flange 16 may include a body-side coupling ring 22 for attaching an ostomy pouch. The body-side coupling ring 22 may be configured to mate with a pouch-side coupling ring (not shown), such that the ostomy pouch may be mechanically secured to the ostomy barrier 10 when the coupling rings are engaged with each other. The flange 16 may be attached to the convex insert 18 via a flange film 30. In the embodiment of FIG. 1, the flange 16 is attached to a pouch-side surface of the flange film 30 proximate an outer periphery of the flange film 30. The convex insert 18 is attached to a body-side surface of the flange film 30 proximate an inner peripheral portion of the flange film 30, such that the flange 16 and the convex insert 18 are attached on the opposite surfaces of the flange film 30 at opposite ends. Such a configuration provides a floating flange feature, in which a user may insert his/her finger between the flange 16 and the convex insert 18 to facilitate engagement of the coupling rings to attach a pouch to the ostomy barrier 10.

The skin barrier 12 may be arranged on the body-side surface of the ostomy barrier 10 for attachment to a user. The inlet opening 28 may be defined by an inner periphery of the skin barrier 12 for receiving a stoma (not shown.) The skin barrier 12 may be formed from a suitable medical-grade adhesive that can adhesively secure the ostomy barrier 10 to a patient's skin in the peristomal region, such as a hydrocolloid adhesive composition.

The ostomy barrier 10 may also include a tape 14 including an adhesive layer 32 and a backing layer 34. In some embodiments, the skin barrier 12 may include a backing layer 36 laminated on the pouch-side surface of the skin barrier 12. The backing layer 36 may be formed from a suitable heat sealable polymeric material, such that the backing layer 36 may be heat sealed to the tape 14.

In the embodiment of FIG. 1, the skin barrier 12 is attached to a portion of the adhesive layer 32 proximate the inlet opening 28 with the backing layer 36 therebetween. In such an embodiment, an outer peripheral portion of the adhesive layer 32 may be attached to a user surrounding the skin barrier 12 to provide additional security.

The adhesive layer 32 of the tape 14 may be formed from a suitable medical adhesive, such as an acrylic adhesive. The backing layer 34 may be formed from a suitable material, such as a nonwoven material or a thin polymeric film.

In other embodiments, the ostomy barrier 10 may not include the tape 14. In such an embodiment, the skin barrier 12 may be the only means for attaching the ostomy barrier 10 to a user.

In the embodiment of FIG. 1, the convex insert 18 is attached to the backing layer 34 of the tape 14 to provide a convexity to the skin barrier 12. In other embodiments, the convex insert 18 may be attached to a pouch-side surface of the skin barrier 12.

Figure 2:
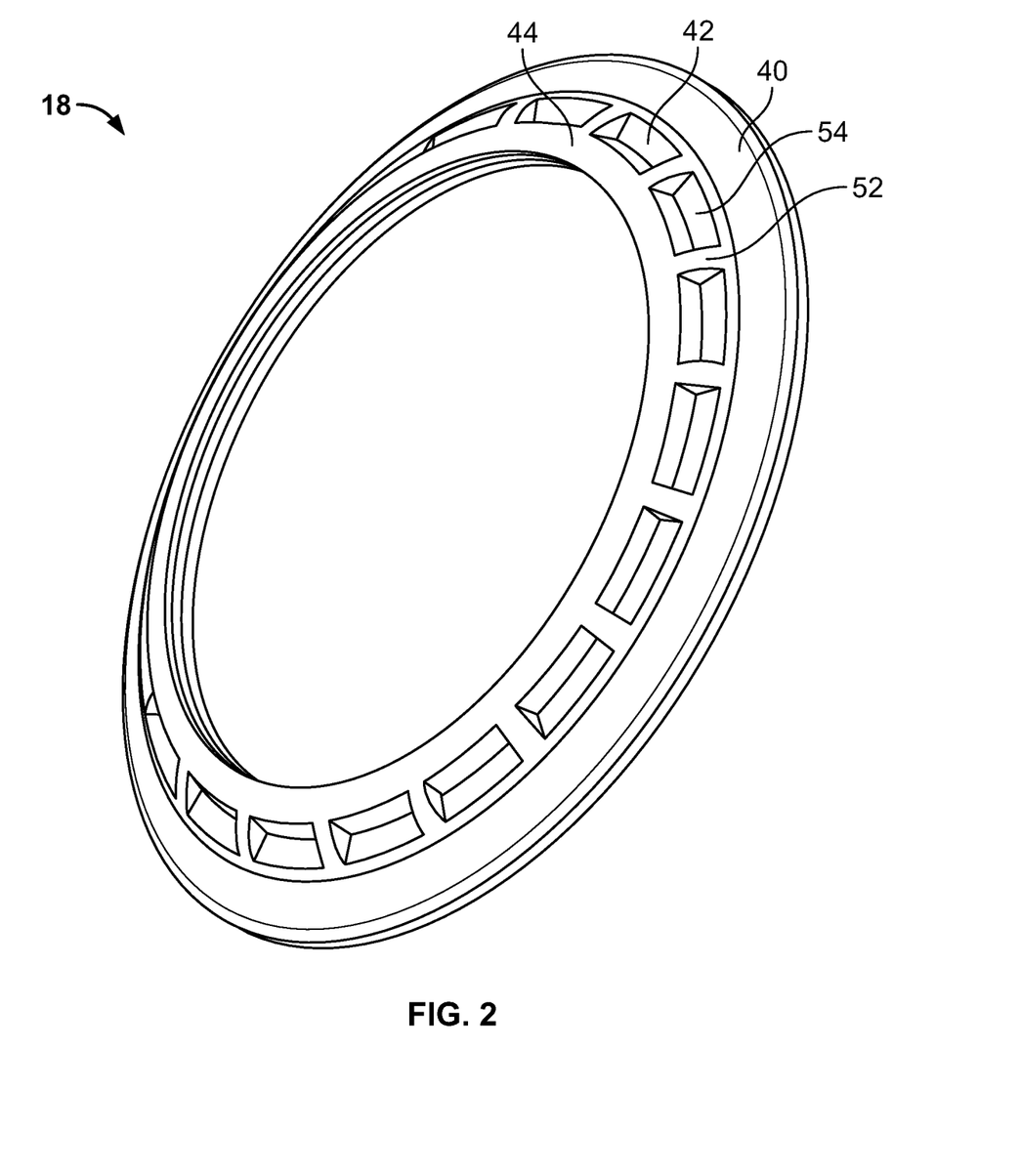
FIG. 2 is a perspective body-side view of a convex insert of the convex ostomy barrier of FIG. 1.
Figure 5:
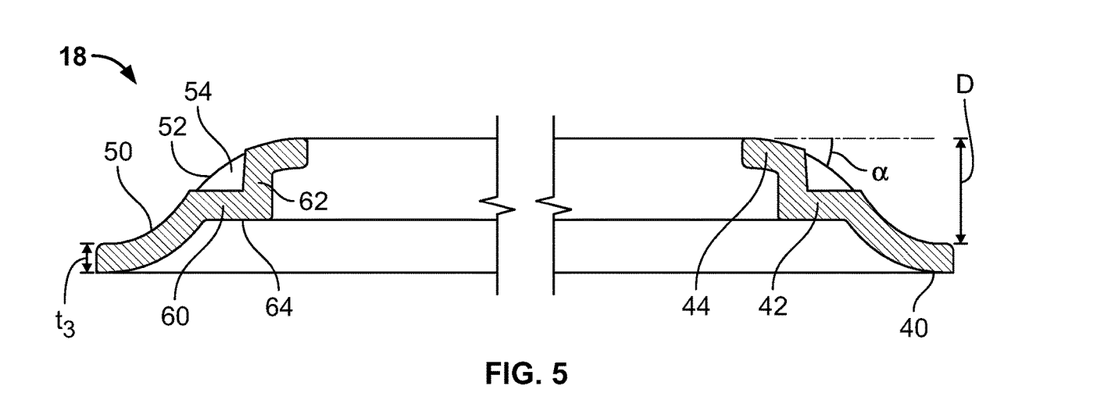
FIG. 5 is a schematic cross sectional view of the convex insert of FIG. 3 taken along A-A.

FIGS. 2-5 are illustrations of the convex insert 18 according to an embodiment. The convex insert 18 may be configured to protrude axially toward a body-side direction as shown in FIGS. 1 and 2 to provide a convex ring-like shaped body configured to apply pressure around the peristomal area when the ostomy barrier 10 is attached to a user. The convex insert 18 may include an outer flange 40, a middle portion 42, and an inner flange 44, and a radial wall 60 providing a generally flat pouch-side surface 64 on a pouch-side of the convex insert 18 for attachment of the flange 16. As best shown in FIGS. 1 and 5, the outer flange 40 may include a concave body-side surface 50, which is configured to conform to a curved contour of a lower base portion 20 of a convex portion of the skin barrier 12.

In this embodiment, the radial wall 60 including the pouch-side surface 64 is provided in the middle portion 42. The middle portion 42 also may include a plurality of core-out windows 54 configured to improve the flexibility of the convex insert 18 and a support structure 52 on the body-side of the convex insert 18 for supporting the skin barrier 12. For example, a plurality of ribs 52 may be provided on the body-side to support the skin barrier 12 as shown in FIGS. 1-5. In this embodiment, the plurality of ribs 52 and the plurality of core-out windows 54 may be arranged, such that adjacent ribs 52 are spaced apart from each other by a core-out window 54 therebetween. Each of the core-out windows 54 may be defined by the radial wall 60, which radially extends from the outer flange 40 toward the inlet opening 28, and an axial wall 62, which axially extends from the radial wall 60 toward a body-side direction, and two adjacent ribs 52. The inner flange 44 may radially extend from the axial wall 62 toward the inlet opening 28 as shown in FIGS. 1 and 5.

In such an embodiment, the middle portion 42 is configured to provide a step-like protrusion in the body-side direction from the outer flange 40 to the inner flange 44. The lengths of the radial wall 60 and/or axial wall 62 may be adjusted to provide a desired convexity angle α and a convexity depth D.

Figure 3:
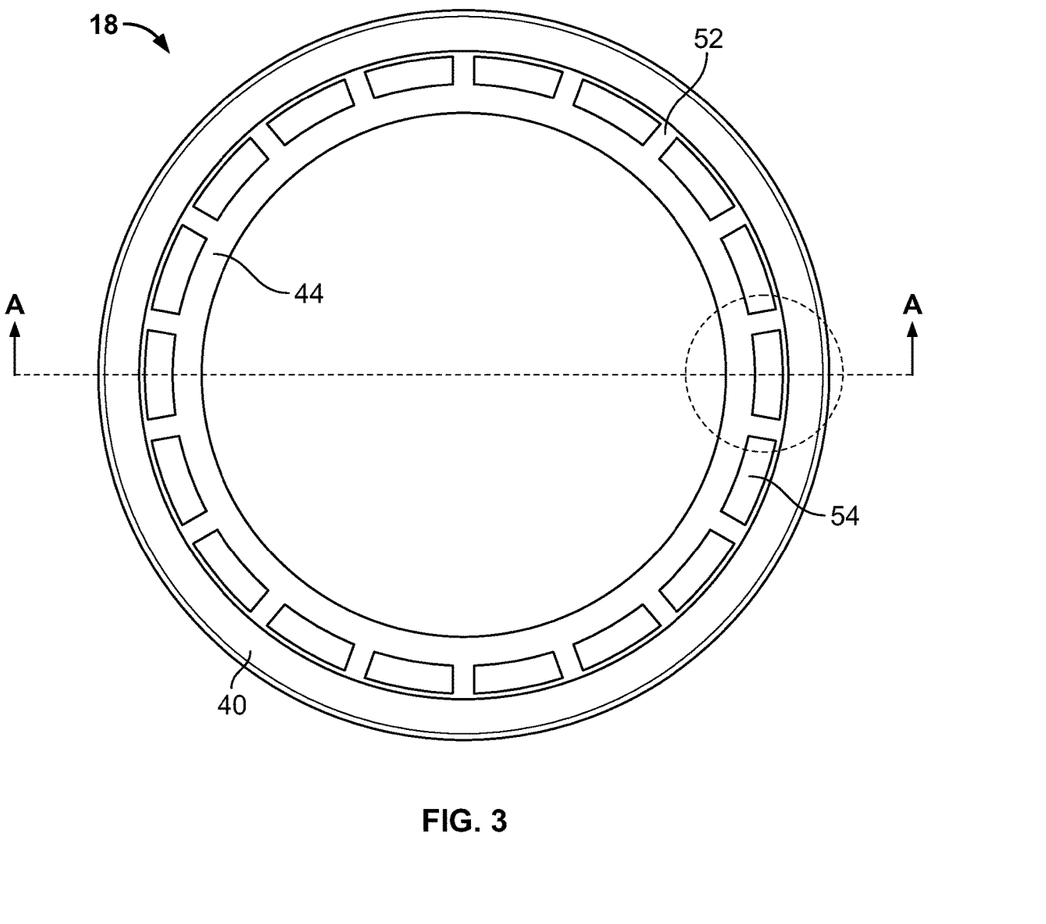
FIG. 3 is a body-side top view of the convex insert of FIG. 2.
Figure 4:
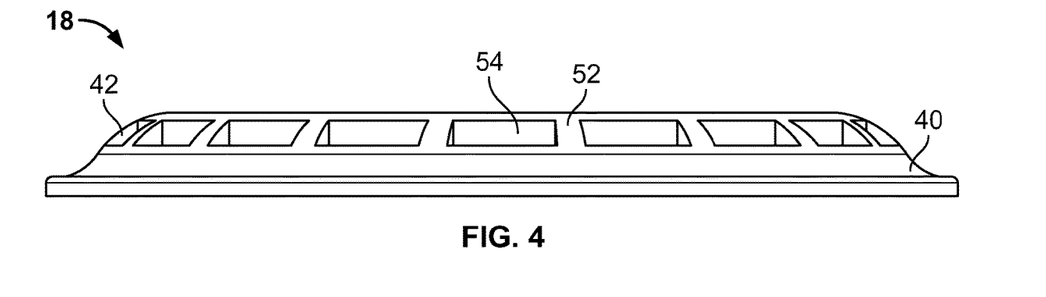
FIG. 4 is a side view of the convex insert of FIG. 2.

The convex insert 18 may be configured to include about 2 ribs to about 50 ribs, preferably about 4 ribs to about 40 ribs, and more preferably to about 8 ribs to about 30 ribs. In the embodiment of FIG. 3, the convex insert 18 includes eighteen ribs. As shown, in FIG. 6, which is an expanded view of the rib 52 and the core-out window 54 of FIGS. 2-5, each of the rib 52 extends from the outer flange 40 to the inner flange 44. The thickness of each of the rib 52 may taper from the outer flange 40 to the inner flange 44, such that an outer thickness $t_1$ may be greater than an inner thickness $t_2$.

Figure 6:
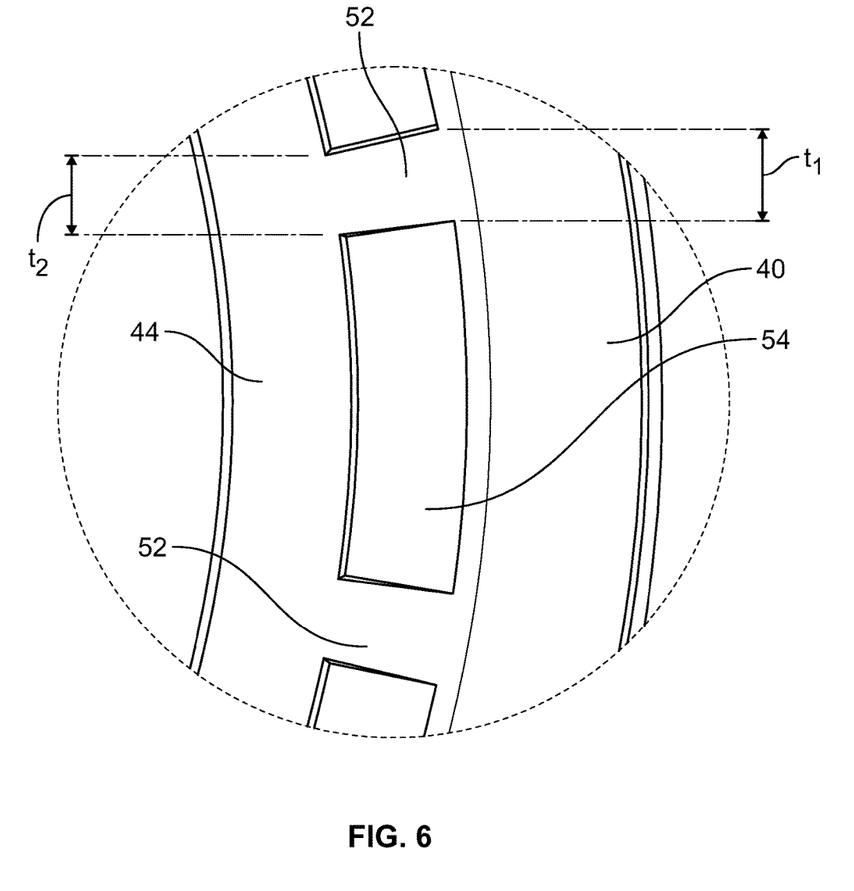
FIG. 6 is a schematic expanded view of a rib and a core-out window of the convex insert of FIG. 2.

In the embodiment of FIG. 6, each of the ribs 52 has an outer thickness $t_1$ of about 0.099 inches and an inner thickness $t_2$ of about 0.082 inches. In another embodiment, each of the rib 52 may be configured to have an outer thickness $t_1$ of about 0.055 inches and an inner thickness $t_2$ of about 0.042 inches. Yet in another embodiment, each of the rib 52 may be configured to have an outer thickness $t_1$ of about 0.037 inches and an inner thickness $t_2$ of about 0.020 inches. The number of ribs and the thicknesses of the ribs may be adjusted to provide a desired flexibility of the convex barrier 10. For example, the number of the ribs and/or the thicknesses of the ribs may be increase to provide a more rigid convex barrier 10. Similarly, the number of the ribs and/or the thicknesses of the ribs may be decreased to prove a more flexible soft convex barrier 10.

In the embodiment of FIG. 1, the flange film 30 may be attached to the pouch-side surface 64 to secure the flange 16 to the convex insert 18. For example, the flange film 30 may be heat sealed to the pouch-side surface 64. As shown in FIG. 1, the body-side surfaces of the outer flange 40, the plurality of ribs 52, and the inner flange 44 may be in contact with the tape 14, wherein at least some portions of which are attached to the backing layer 34. For example, the body-side surface of the outer flange 40 may be heat sealed to the backing layer 34 of the tape 14. In another example, an adhesive may be applied on the body-side surface of the convex insert 18 for attachment of the tape 14.

The convex insert 18 may be formed from a suitable material, such as polymeric materials, rubber, silicone, or metallic materials. For example, the convex insert 18 may be formed from a heat sealable thermoplastic material, such as ethylene vinyl acetate (EVA), thermoplastic elastomer, or thermoplastic urethane. In another example, the convex insert 18 may be formed from a foam or silicone. The convex insert 18 may be formed via thermoforming or other known methods. The convex insert 18 may be configured to have a thickness $t_3$ of about 0.015 inches to about 0.150 inches, preferably about 0.025 inches to about 0.100 inches, and more preferably about 0.030 inches to about 0.080 inches. In the embodiment of FIG. 5, the convex insert 18 is configured to have a thickness $t_3$ of about 0.065 inches. In another embodiment, the convex insert 18 is configured to have a thickness $t_3$ of about 0.050 inches. In yet another embodiment, the convex insert 18 is configured to have a thickness $t_3$ of about 0.035 inches.

A release liner may be provided to cover the skin barrier 12 and the tape 14. In the embodiment of FIG. 1, the release liner 24 is provided to cover an outer peripheral portion of the tape 14, and the release liner 26 is provided to cover the entire body-side surface of the ostomy barrier 10 including the skin barrier 12 and the tape 14. In use, the release liner 26 may be removed first for attachment of the skin barrier 12 to peristomal skin, and the release liner 24 may be removed subsequently to expose the tape 14 for further attachment to user's skin.

Figure 7:
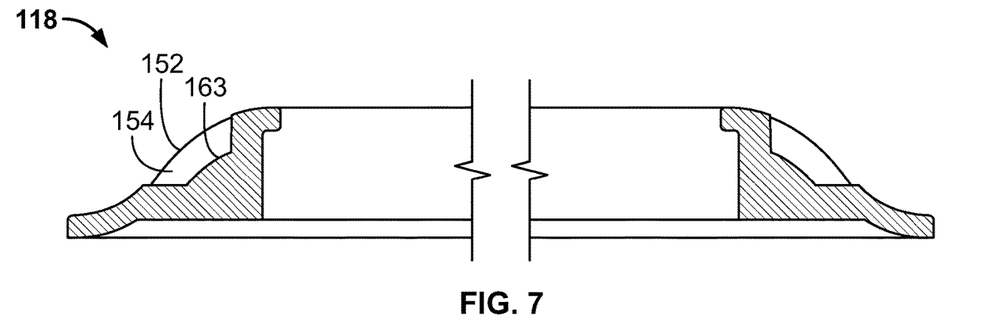
FIG. 7 is a schematic cross section view of a convex insert according another embodiment.

In the convex insert 18 of FIGS. 1-5, body-side surfaces of the radial wall 60 and the axial wall 62 are generally flat, such that an intersection of the radial wall 60 and the axial wall 62 forms a generally 90° angle. In other embodiments, a body-side surface of the plurality of core-out windows 18 may be curved proximate the intersection. FIG. 7 is a cross sectional view of a convex insert 118 including a plurality of core-out windows 154 having a curved body-side surface 163 according to an embodiment. In this embodiment, the curved body-side surface 163 provides a convex contour similar to the convex outer contour of the ribs 152. In another embodiment, the body-side surfaces of the radial wall 60 and the axial wall 62 may from a one continuous concave surface similar to the concave body-side surface 50 of the outer flange 40.

Figure 8:
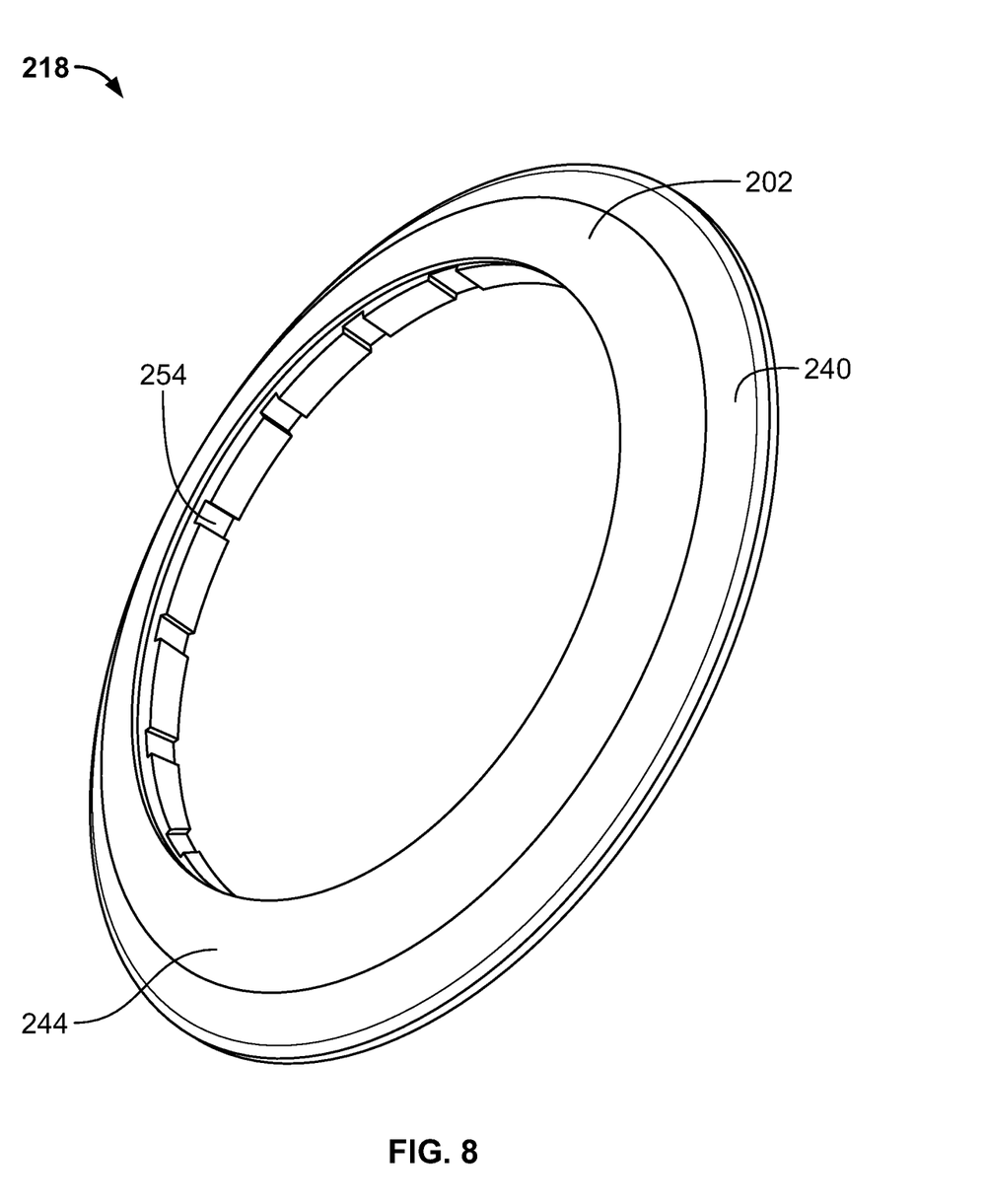
FIG. 8 is a perspective body-side view of a convex insert according to yet another embodiment.
Figure 9:
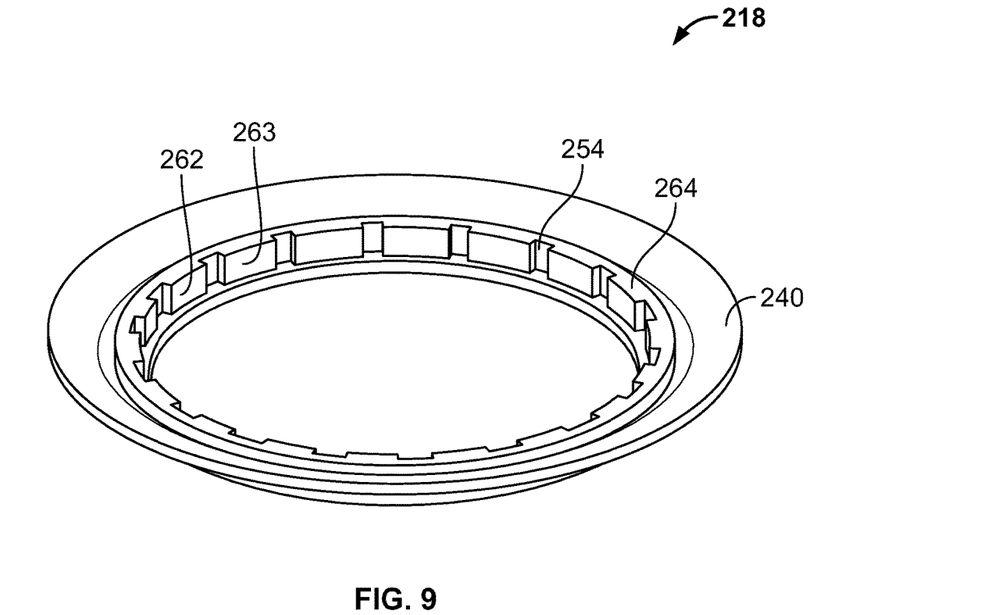
FIG. 9 is a perspective pouch-side view of the convex insert of FIG. 8.
Figure 10:
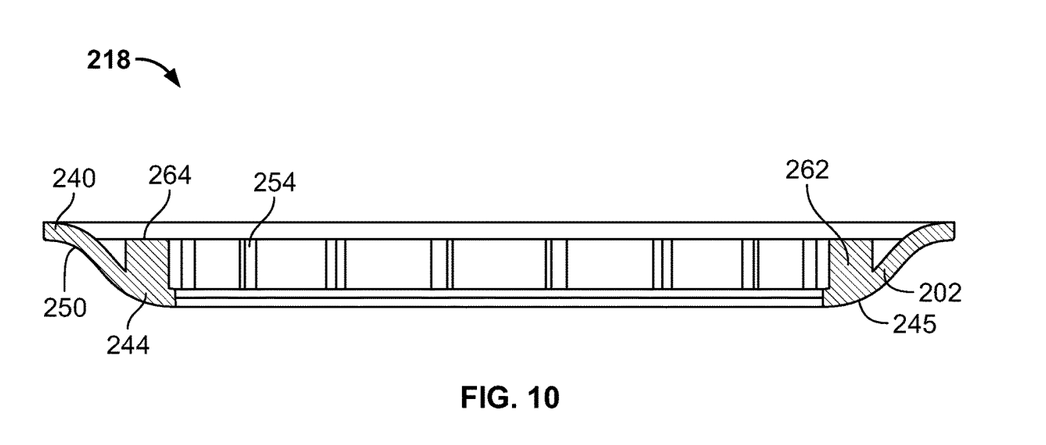
FIG. 10 is a schematic cross sectional view of the convex insert of FIG. 8.

FIGS. 8-10 illustrate a convex insert 218 according to yet another embodiment. The convex insert 218 may have convex ring-like shaped body 202 including an outer portion 240 and a convex inner portion 244. As it was with the convex inserts 18, 118, the convex insert 218 may be configured to protrude axially toward a body-side direct as shown in FIGS. 8 and 10 to provide the convex ring-like shaped body. The outer portion 240 may include a concave body-side surface 250, while the inner portion 244 may include a convex body-side surface 245. The convex insert 218 may also include an axial wall 262 axially extending from a pouch-side surface of the inner portion 244 forming a cylindrical wall structure and a pouch-side surface 264 for attachment of a flange 16 as best shown in FIG. 9. A plurality of windows 254 may be provided along an inner surface 263 of the axial wall 262.

Figure 11:
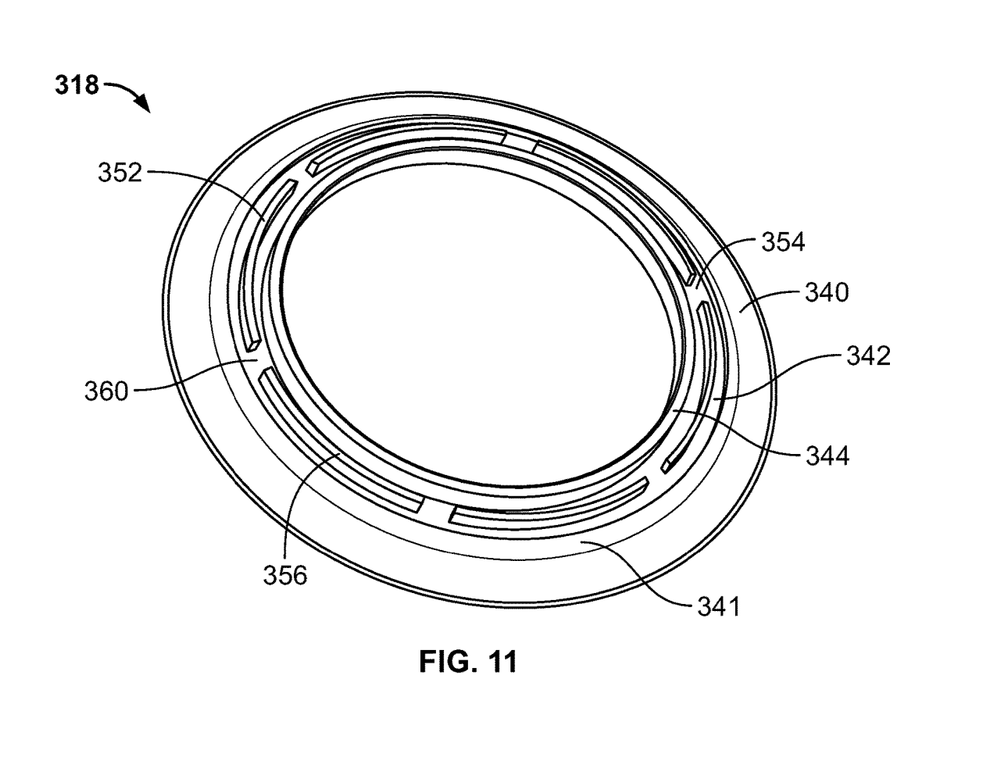
FIG. 11 is a perspective body-side view of a convex insert according to an embodiment.
Figure 12:
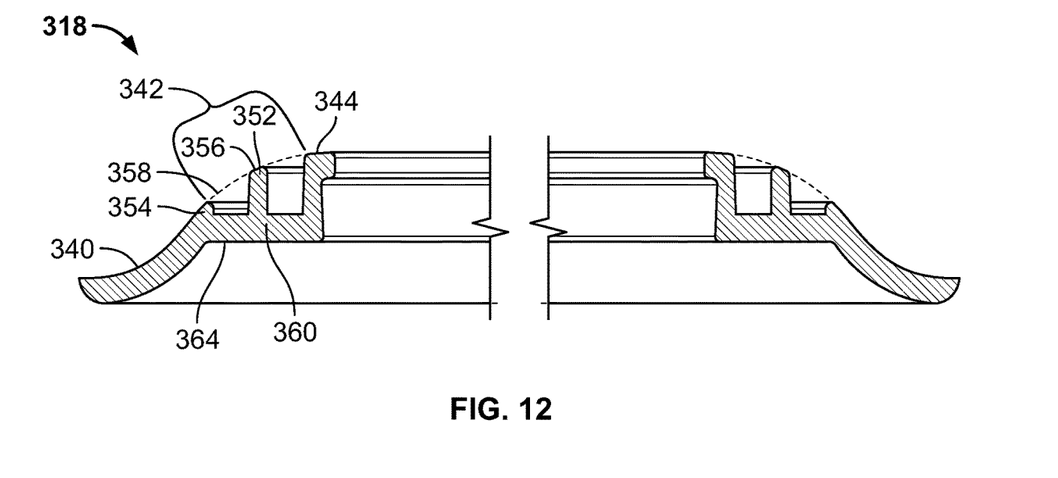
FIG. 12 is a schematic cross sectional view of the convex insert of FIG. 11.
Figure 13:
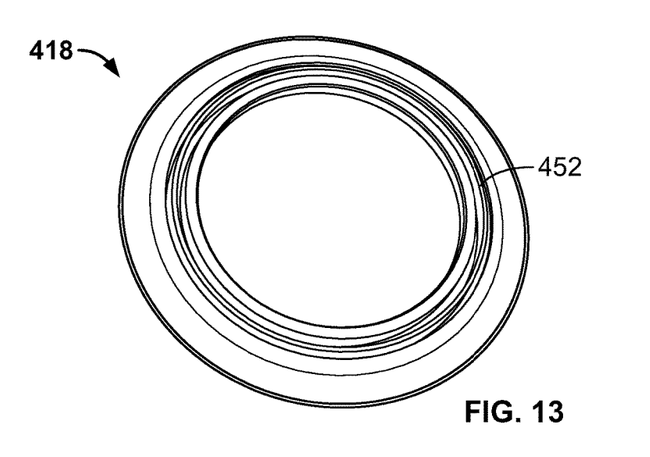
FIGS. 13-21 are perspective views of convex inserts according to various embodiments.
Figure 14:
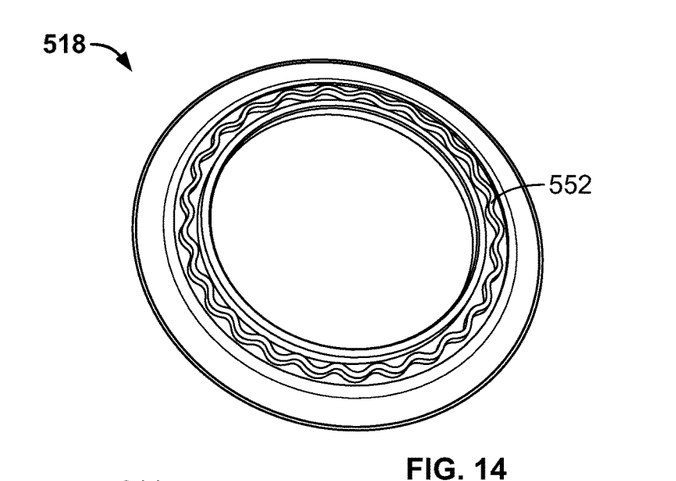

FIGS. 11 and 12 are illustrations of a convex insert 318 according to an embodiment. The convex insert 318 may be configured similar to the convex insert 18 of FIGS. 1-5 including a convex ring-like shaped body for applying pressure around the peristomal area when the ostomy barrier 10 is attached to a user. The convex insert 318 may comprise an outer flange 340, a middle portion 342, and an inner flange 344. The middle portion may include a radial wall 360 providing a generally flat pouch-side surface 364 for attaching a flange 16, core-out portions 354 configured to improve the flexibility of the convex insert 318, and a plurality of support structures 352 protruding axially from a body-side surface of the radial wall 360 for supporting a skin barrier 12. In this embodiment, the plurality of support structures 352 forms a split ring-like shape as shown in FIG. 11. The outer flange 340 may extend beyond the radial wall 360 to form a protrusion 341, and each of the plurality of support structures 352 may include a sloped surface 356, such that the inner flange 344, the plurality of support structures 352 and the protrusion 341 may provide a concave line of support 358 shown in phantom lines in FIG. 12 for the skin barrier 12.

FIGS. 13-21 are illustrations of convex inserts according to various embodiments. These convex inserts are configured similar to the convex inserts 18, 318 having a convex ring-like shaped body and generally include an outer flange, a middle portion, and an inner flange. The middle portion may include a generally flat pouch-side surface for attaching a flange, core-out portions, and a support structure on the body side for supporting a skin barrier. The support structure of these embodiments may be provided in various shapes and forms. For example, the convex insert 418 of FIG. 13 may include a support structure 452 that is configured similar to the support structure 352 of FIG. 11, except the support structure 452 is provided as a single continuous ring-like structure. A support structure 552 of the convex insert 518 of FIG. 14 may be configured similar to the support structure 452 of FIG. 13, except the support structure 552 is provides as a wavy ring-like structure.

Figure 15:
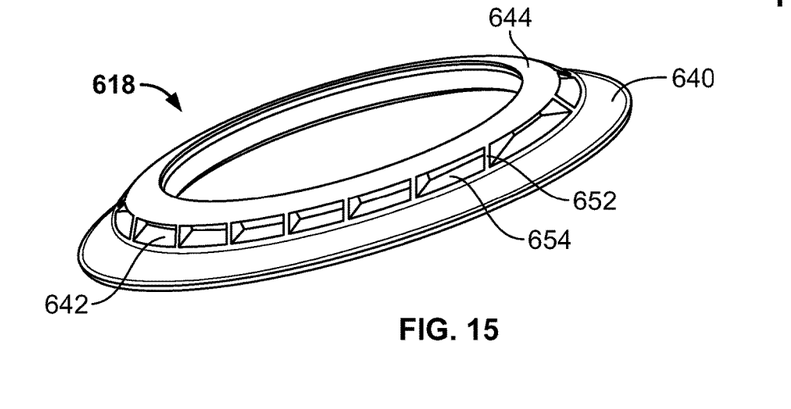

The convex insert 618 of FIG. 15 may be configured similar to the convex insert 18 generally comprising an outer flange 640, a middle portion 642, an inner flange 644, a generally flat pouch-side surface for attachment of a flange and a plurality of support structures 652 for supporting a skin barrier. In this embodiment, the plurality support structures 652 may be provided as rib-like structures defined between a plurality of core-out windows 654, which may undercut below the inner flange 644 to provide core-out portions thereunder.

Figure 16:
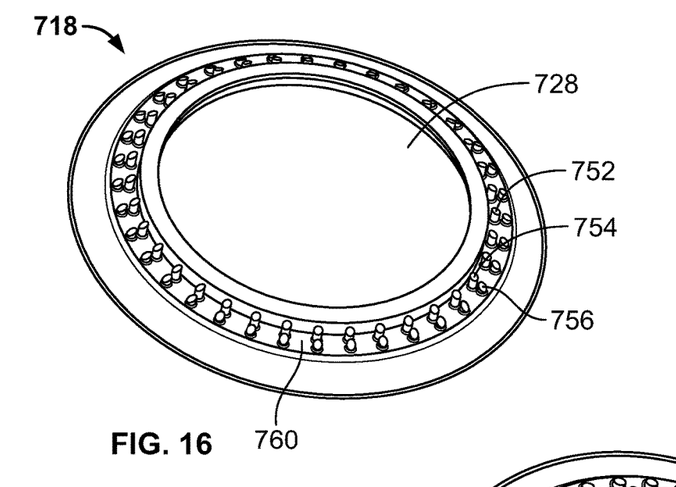
Figure 17:
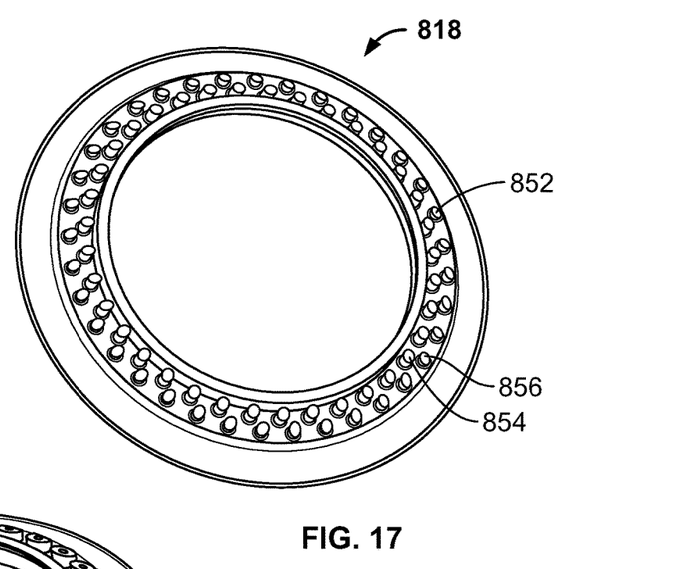

The convex insert 718 of FIG. 16 may comprise a plurality of support structures 752 axially extending from a radial wall 760. The plurality of support structures 752 may include a plurality of taller rod-like structures 754 and a plurality of shorter rod-like structures 756. In this embodiment, the convex insert 718 may include the same number of the taller rod-like structures 754 and the shorter rod-like structures 756. The taller rod-like structures 754 may be arranged in a circle concentric to an inlet opening 728, while the shorter rod-like structures 756 may be arranged in a circle surrounding the taller rod-like structures 754 and concentric to the inlet opening 728. Further, the taller rod-like structures 754 and the shorter rod-like structures 756 may be aligned radially in pairs as shown in FIG. 16. The each of the taller rod-like structures 754 and the shorter rod-like structures 756 may include a sloped body-side surface configured to provide a support for a skin barrier 12 similar to the plurality of support structures 356 of FIGS. 11 and 12. The convex insert 818 of FIG. 17 may include a plurality of support structures 852 configured similar to the plurality of support structures 752 of FIG. 16, except taller rod-like structures 854 and shorter rod-like structures 856 are staggered and are not radially aligned in pairs.

Figure 18:
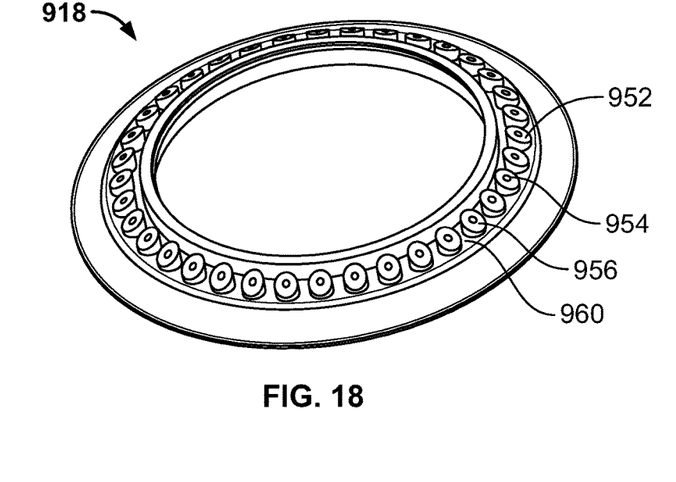
Figure 19:
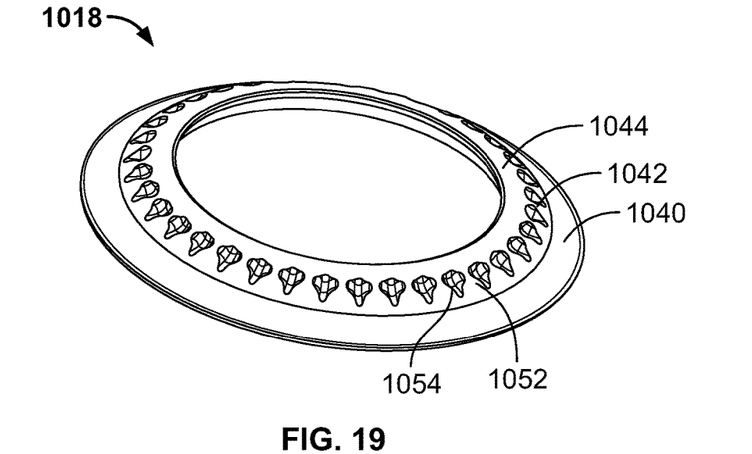
Figure 20:
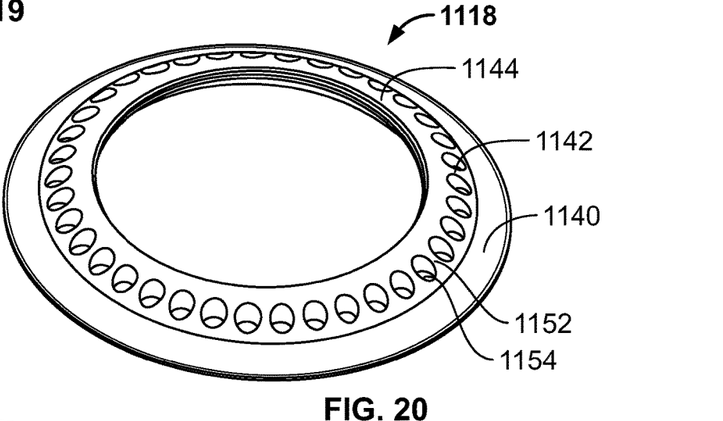
Figure 21:
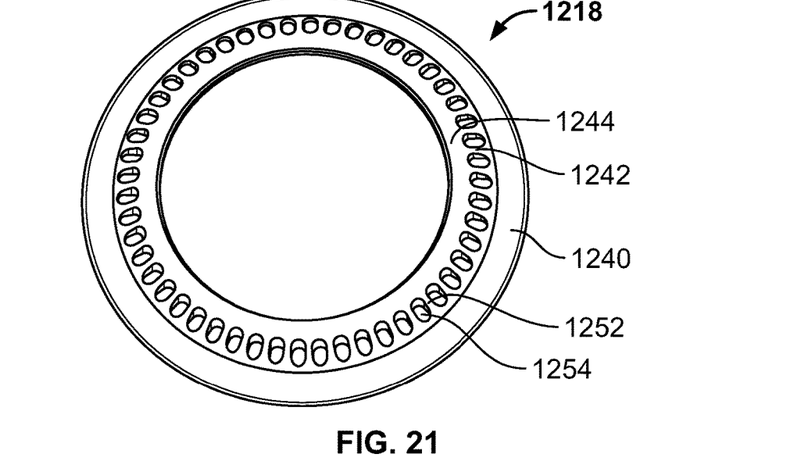

The convex insert 918 of FIG. 18 may comprise a plurality of support structures 952 axially extending from a radial wall 960, each of which having a tube-like body including an opening 954 and a sloped body-side surface 956 for supporting a skin barrier 12. The convex inserts 1018, 1118, 1218 of FIGS. 19-21 are similarly configured comprising an outer flange 1040, 1140, 1240, a middle portion 1042, 1142, 1242, an inner flange 1044, 1144, 1244, a generally flat pouch-side surface for attachment of a flange, a plurality of core-out portions 1054, 1154, 1254, and a support structure 1052, 1152, 1252 defined therebetween for supporting the skin barrier 12.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A convex ostomy barrier assembly for attaching an ostomy appliance to a peristomal skin surrounding a stoma, the convex ostomy barrier assembly comprising:
   a skin barrier comprising an adhesive;
   an inlet opening for receiving a stoma;
   a convex insert arranged adjacent the skin barrier, the convex insert having a convex ring-shaped body and comprising:
      an inner flange;
      a middle portion including a pouch-side surface, a core-out portion, and a skin barrier support structure for supporting the skin barrier; and
      an outer flange, wherein the inner flange and the outer flange are connected by the middle portion and arranged in different axial planes to define the convex ring-shaped body,
      wherein the middle portion comprises a radial wall having the pouch-side surface radially and directly extending from the outer flange toward the inlet opening, and an axial wall extending axially from the radial wall in a body-side direction, wherein the inner flange extends from the axial wall toward the inlet opening, wherein the outer flange, the middle portion, and the inner flange provide a protrusion in the body-side direction, and wherein the pouch-side surface is defined on a pouch-side of the radial wall and located axially between the inner flange and an outer periphery of the outer flange; and a flange including a body-side coupling ring attached to the pouch-side surface of the convex insert.

2. The convex ostomy barrier assembly of claim 1, wherein the skin barrier support structure includes a plurality of support structures extending axially from a body-side of the radial wall; wherein the plurality of support structures form a split ring shape, wherein each of the plurality of support structures is surrounded by the core-out portion and includes a sloped body-side surface configured to support the skin barrier having a convex body-side surface.

3. The convex ostomy barrier assembly of claim 1, wherein the core-out portion is defined by a plurality of core-out windows, and the skin barrier support structure includes a plurality of ribs, wherein the plurality of core-out windows and the plurality of ribs are arranged such that adjacent ribs are spaced apart from each other by a core-out window therebetween, and each of the core-out windows is defined by the radial wall, the axial wall, and the adjacent ribs.

4. The convex ostomy barrier assembly of claim 3, wherein the convex insert includes about 8 ribs to about 30 ribs.

5. The convex ostomy barrier assembly of claim 1, wherein the convex ostomy barrier assembly includes a tape, wherein the convex insert is attached to a pouch-side of the tape, and the skin barrier is attached to a body-side of the tape, wherein the outer flange has a concave body-side surface configured to conform to a curved contour of a lower base section of a convex portion of the convex ostomy barrier assembly.

6. The convex ostomy barrier assembly of claim 5, wherein at least some portion of a body-side surface of the outer flange, the skin barrier support structure, or a body-side surface of the inner flange is attached to the tape.

7. The convex ostomy barrier assembly of claim 6, wherein at least the body-side surface of the outer flange is heat sealed to the tape.

8. The convex ostomy barrier assembly of claim 1, wherein the pouch-side surface of the middle portion is a flat surface defined on the pouch-side of the radial wall, wherein the flange is attached to the convex insert via a flange film, and wherein the flange film is attached to the pouch side surface.

9. The convex ostomy barrier assembly of claim 8, wherein the flange film is heat sealed to the pouch side surface.

10. A convex insert for an ostomy barrier having a convex ring-shaped body and comprising:
an inlet opening;
an inner flange;
a middle portion including a pouch-side surface, a core-out portion, and a skin barrier support structure, wherein the core-out portion is configured to improve flexibility of the convex insert; and
an outer flange, wherein the inner flange and the outer flange are connected by the middle portion and arranged in different axial planes to define the convex ring-shaped body,
wherein the middle portion comprises a radial wall having the pouch-side surface radially and directly extending from the outer flange toward the inlet opening, and an axial wall extending axially from the radial wall in a body-side direction, wherein the inner flange extends from the axial wall toward the inlet opening, wherein the outer flange, the middle portion, and the inner flange provide a protrusion in the body-side direction, and wherein the pouch-side surface is defined on a pouch-side of the radial wall and located axially between the inner flange and an outer periphery of the outer flange.

11. The convex insert of claim 10, wherein the skin barrier support structure includes a plurality of support structures extending axially from a body-side of the radial wall; wherein the plurality of support structures form a split ring shape, wherein each of the plurality of support structures is surrounded by the core-out portion and includes a sloped body-side surface.

12. The convex insert of claim 10, wherein the core-out portion is defined by a plurality of core-out windows, and the skin barrier support structure includes a plurality of ribs, wherein the plurality of core-out windows and the plurality of ribs are arranged such that adjacent ribs are spaced apart from each other by a core-out window therebetween, and each of the core-out windows is defined by a radial wall, an axial wall, and the adjacent ribs.

13. The convex insert of claim 10, wherein the skin barrier support structure includes a ring-shaped structure extending axially from a body-side of the radial wall, wherein the core-out portion is defined by two ring-shaped core-out portions, and wherein the skin barrier support structure is arranged between the two ring-shaped core-out portions and has a sloped body-side surface.

14. The convex insert of claim 10, wherein the skin barrier support structure includes a plurality of rod-like structures extending axially from a body-side of the radial wall.

15. The convex insert of claim 10, wherein the skin barrier support structure includes a plurality of tube-like structures extending axially from a body-side surface of the radial wall.

16. The convex insert of claim 10, wherein the core-out portion is defined by a plurality of openings in the middle section, and the skin barrier support structure is defined by a body-side surface of the middle section between the plurality of openings.

* * * * *